United States Patent [19]
Arita et al.

[11] Patent Number: 5,971,922
[45] Date of Patent: Oct. 26, 1999

[54] SYSTEM AND METHOD FOR PREDICTING BLOOD GLUCOSE LEVEL

[76] Inventors: Seizaburou Arita, 6-2-2804, Takenodai 6-chome, Nishi-ku, Kobe-shi, Hyogo, Japan, 651-2274; Masaya Yoneda, 2034-16 Tsudakadai 2-chome, Okayama-shi, Okayama, Japan, 701-1151; Tadashi Iokibe, c/o Kabushiki Kaisha Meidensha 1-17, Osaki 2-chome, Shinagawa-ku, Tokyo, Japan, 141-0032

[21] Appl. No.: 09/174,258

[22] Filed: Oct. 16, 1998

[30] Foreign Application Priority Data

Apr. 7, 1998 [JP] Japan ................................. 10-093783

[51] Int. Cl.$^6$ ........................................... A61B 5/05
[52] U.S. Cl. ............................ 600/365; 600/300; 706/58; 706/45
[58] Field of Search .................................. 600/365, 319, 600/300, 301; 706/58, 45

[56] References Cited

U.S. PATENT DOCUMENTS

| | | | |
|---|---|---|---|
| 4,731,726 | 3/1988 | Allen, III .............................. | 364/416 |
| 5,251,126 | 10/1993 | Kahn et al. .......................... | 364/413.11 |
| 5,748,851 | 5/1998 | Iokibe et al. .............................. | 706/58 |

*Primary Examiner*—Cary O'Connor
*Assistant Examiner*—Navin Natnithithadha

[57] ABSTRACT

A system for predicting a blood glucose level is comprised of a time series measurement data storing section for storing blood glucose level measured data in a blood glucose time series file to treat the data as time series data. A dynamics estimating section estimates a dynamics which most preferably represents a phase characteristic of the time series data stored in the time series measurement data storing section. A parameter storing section stores an embedding dimension n and a time delay τ of the dynamics estimated in the dynamics estimating section as parameters for embedding the estimated dynamics in multidimensional state space. A blood glucose predicting section predicts a near future value of blood glucose level by means of the Local Fuzzy Reconstruction Method on the basis of the stored data of the blood glucose level data stored in the blood glucose time series file and the parameters corresponding to the data and for storing the predicted future value in a predicted blood glucose level file. A display section displays the data of the blood glucose time series file and the predicted blood glucose level file.

6 Claims, 8 Drawing Sheets

SYSTEM AND METHOD FOR PREDICTING BLOOD GLUCOSE LEVEL

BACKGROUND OF THE INVENTION

The present invention relates to a system and method for predicting blood glucose level by means of computer analysis of blood glucose time-series data of a diabetic.

Basically, insulin therapies for diabetics are executed by applying insulin calculated based on a blood glucose level of a patient (diabetic). The control of blood glucose level is mainly executed by an open circle method in that the blood glucose level is simply measured or by a feedback method in that an insulin administration amount is determined on the basis of the blood glucose level measurement data by a doctor once or twice a month. Furthermore, in some cases, the insulin administration amount is controlled day by day on the basis of a predetermined insulin scale. Doctors mainly have executed insulin treatments to patients as follows. (1) On the basis of the blood glucose level measurement date, the doctor determines the insulin administration amount twice a month. (2) On the basis of the predetermined insulin administration amount to the blood glucose level, the insulin is applied to a patient one or third a day.

However, these treatments may put the blood glucose level unstable since they include a feedback having a large time lag. For example, the increase of the insulin administration amount for decreasing the average of the blood glucose level may invite low blood glucose level (hypoglycemia). On the other hand, the decrease of the insulin administration amount may invite high blood glucose level (hyperglycemia). Therefore, in order to properly determine the insulin administration amount for a proper blood glucose level control, it is necessary to execute a blood glucose level control without time lag so as to decrease a daily change of the blood glucose level and to finally put it within an allowable range.

SUMMARY OF THE INVENTION

It is an object of the present invention to provide a system and method for predicting blood glucose level which system and method enables a determination of a proper insulin administration amount without time lag, and a prediction of a daily blood glucose on the basis of the blood glucose level measured data.

The inventors of the present invention propose a method and system for enabling a short-term prediction of the blood glucose level from a present blood glucose by means of the Local Fuzzy Reconstruction Method disclosed in U.S. Pat. No. 5,748,851.

An aspect of the present invention resides in a blood glucose level predicting system which comprises a time series measurement data storing section for storing blood glucose level measured data in a blood glucose time series file to treat the data as time series data, a dynamics estimating section for estimating a dynamics which most preferably represents a phase characteristic of the time series data stored in the time series measurement data storing section, a parameter storing section for storing embedding a dimension n and a time delay τ of the dynamics estimated in the dynamics estimating section as parameters for embedding the estimated dynamics in multidimensional state space, a blood glucose predicting section for predicting a near future value of the blood glucose level by means of the Local Fuzzy Reconstruction Method on the basis of the stored data of the blood glucose level data stored in the blood glucose time series file and the parameters corresponding to the data and for storing the predicted future value in a predicted blood glucose file, and a display section for displaying the data of the blood glucose time series file and the predicted blood glucose file.

Another aspect of the present invention resides in a blood glucose level predicting method which comprises the steps of: preparing blood glucose level data measured at latest and past time for use as time series data; constructing an attractor by embedding the time series data in a multidimensional space according to the Takens' Embedding Theorem; selecting data vector z(T) on the attractor which includes the latest blood glucose data; selecting a plurality of neighboring vectors x(i) on the other trajectory passing through a neighbor space of the data vector z(T) on the basis of a selecting reference that the Euclidean distance is smaller than a predetermined value; selecting a data vector x(i+s) at s steps future with respect to the data vector x(i) from the attractor; estimating a predicted value z(T+s) at s steps future with respect to the data vector z(T) by using the data vectors z(T), x(i) and x(i+s) by means of the Local Fuzzy Reconstruction Method; and obtaining a predicted value y(T+s) at s step future with respect to the predicted value z(T+s).

DETAILED DESCRIPTION OF THE INVENTION

The inventors of the present invention found that the time series behavior of the blood glucose level performs a chaotic phenomenon, on the basis of the analysis as to the instability of the blood glucose level control. Further, they proposed a method and system for enabling a short-term prediction of the blood glucose level from a present blood glucose level by means of the Local Fuzzy Reconstruction Method disclosed in U.S. Pat. No. 5,748,851 which has been proposed by the inventors of this invention.

(Time Series Behavior and Chaotic Phenomena of Blood Glucose Level)

First, as to time series behavior and chaotic phenomena of blood glucose level, the analyzed and proved contents will be discussed hereinafter.

Figure 2A:
FIGS. 2A to 2C are graphs each of which shows a part of time series data of cases I, II and III.
Figure 2B:
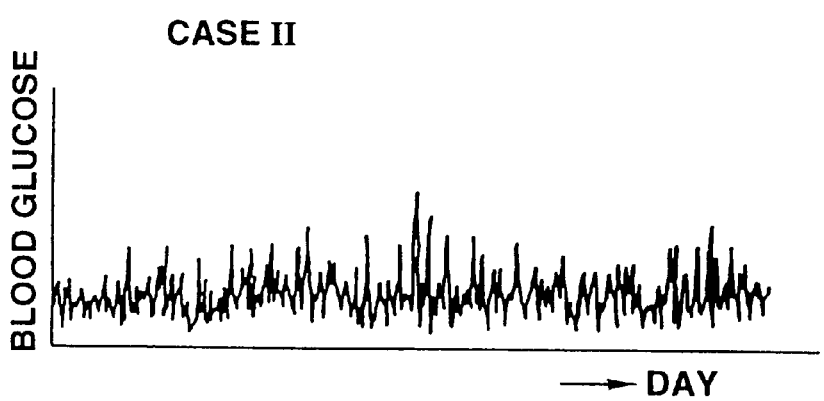
Figure 2C:
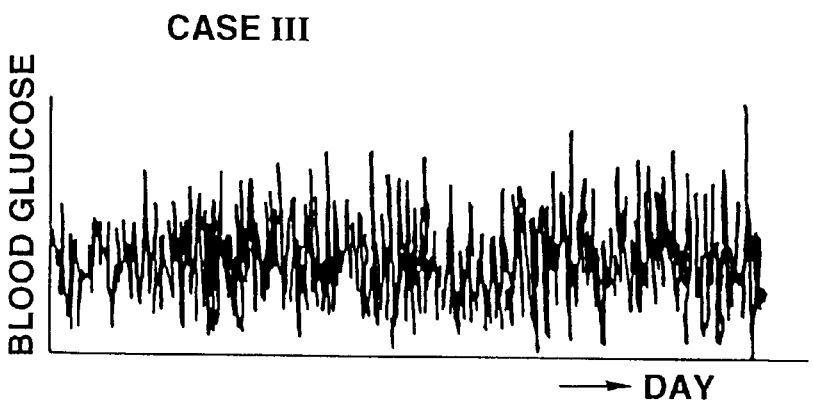

The analyzed objects of the blood glucose level were ten diabetics including five cases of insulin dependency type (IDDM) and five cases of non-insulin dependency type (NIDDM). The data thereof were recorded day by day for at least one year and a half and for at most ten years. FIGS. 2A to 2C show time series data of one NIDDM case and two IDDM cases which were put in a good control condition.

A percentage of $HbA_{1c}$ is employed as an index of a practical control since it is practically known that the percentage of $HbA_{1c}$ generally represents an average of the controlled blood glucose level for the past one or two month. The percentage of $HbA_{1c}$ of the case I was stably controlled within a range from 5 to 6% as shown in FIG. 2A. The percentage of $HbA_{1c}$ of the case II was similarly controlled within a range from 5 to 6% as shown in FIG. 2B. The percentage of $HbA_{1c}$ of the case III was controlled within a range from 9 to 11% as shown in FIG. 2C.

The case I is diagnosed to have a non insulin dependent type diabetes, so that the blood glucose level control function is insufficiently executed by means of intrinsic insulin secretion. The cases II and III are diagnosed to have an insulin dependent type diabetes, so that intrinsic insulin secretion is almost not executed and therefore the blood glucose level control function due to the intrinsic insulin secretion almost does not executed.

By executing the spectrum analysis as to the data of these three cases by means of FFT (Fast Fourier Transform), each of frequency components appeared in wide range. The self-correlation function of each frequency component was converged to nearly zero according to the increase of time. The maximum Lyapunov exponent thereof was positive. These results represented that there was a possibility that these three cases perform chaotic behaviors.

Figure 3A:
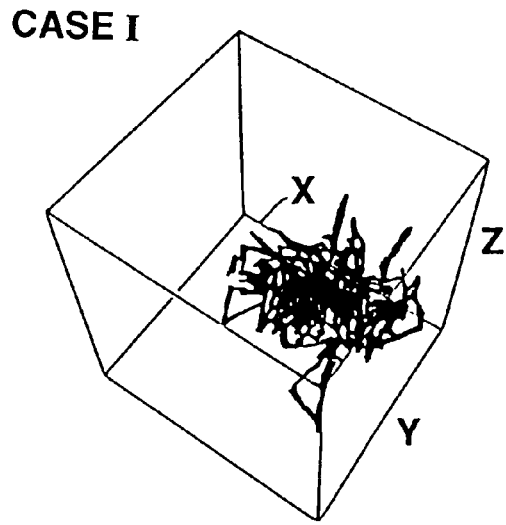
FIGS. 3A to 3C are perspective views of attractors of FIGS. 2A to 2C projected on the three dimensional space.
Figure 3B:
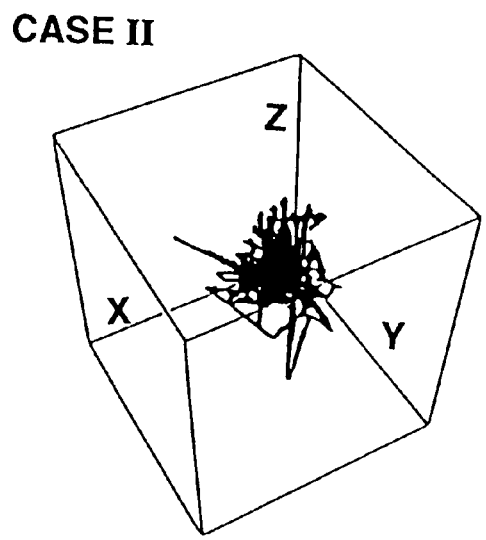
Figure 3C:
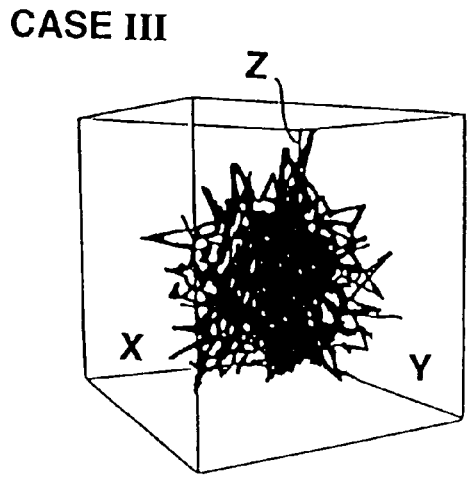

FIGS. 3A to 3C show attractors projected on the three-dimensional space as to the three cases. The attractor of the case I had a cylindrical shape, the attractor of the case II had a tetrahedron shape, and the attractor of the case III had a ball shape. As to fractal dimension, the case I was 2.27, the case II was 2.73, and the case III was 3.54. This represented that the fractal dimension increased according to the complexity of the shape of the attractor.

As a result of the evaluation of the control level of the blood glucose level by $HbA_{1c}$, the evaluation of the cases I (cylindrical shape) and II (tetrahedron shape) were good control similarly. It was deemed that the difference of the shapes of the attractors was caused by the difference of the self blood glucose level control ability between IDDM and NIDDM. Both of the cases II and III were IDDM and were controlled by the continuous insulin subcutaneous injection treatment (CSII). The control level of the case II was good control, and that of the case III was poor control.

The result of the researches as to the other cases represented that all of them perform chaotic behaviors. The shapes of the attractors thereof were one of a cylindrical shape, a tetrahedron shape, a ball shape, or mixture thereof.

Figure 4:
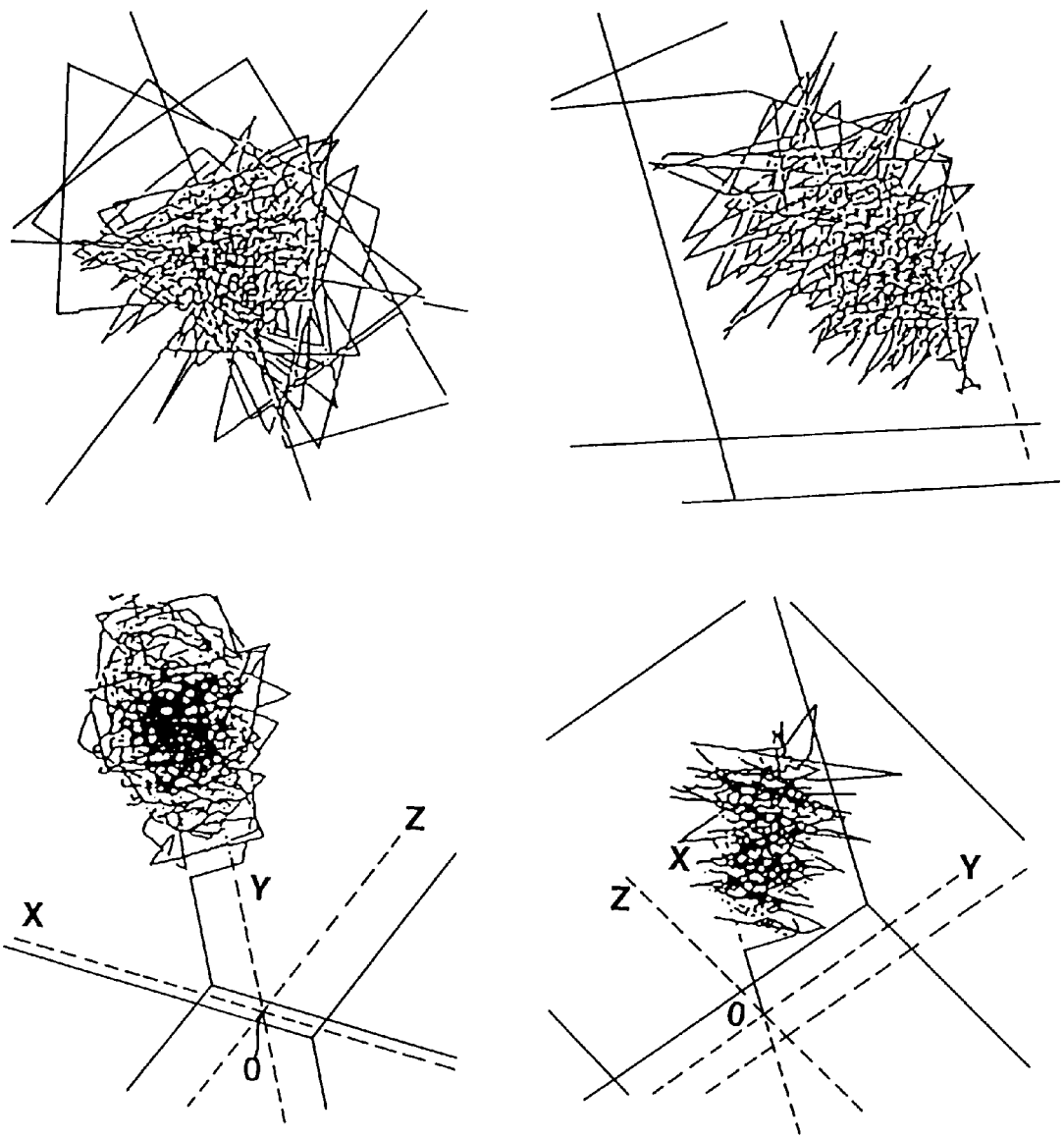
FIG. 4 is views showing detailed shape of the attractors on the three dimensional space.

As a result of the various researches in view of the variation of the number of data and in the various viewpoints, it was deemed that the attractors of the three shapes were formed based on a spiral shape shown in FIG. 4 and the spiral shape is changed into one of the cylindrical shape, the tetrahedron shape and the ball shape according to several parameters and noises. Further, it was inferred that the parameters would be dependent on the remaining of the blood glucose level control ability by means of the intrinsic insulin secretion and the control level of the blood glucose level from the other cases.

As mentioned above, although the time series behavior of the blood glucose level of diabetics is deemed to be irregular phenomena which were considered as indeterministic phenomena subordinated to randomness, it was solved that the time series behavior of the blood glucose level is a deterministic chaos phenomenon which is governed by a distinct determinism.

(Blood Glucose Level Prediction by Local Fuzzy Reconstruction Method)

When the behavior of any time series data is chaotic, it can be assumed that the behavior follows a certain deterministic law. Then, if the nonlinear deterministic regularity can be estimated, data in the near future until losing the deterministic causality can be predicted from the observed data at a certain time point because chaos has a sharp dependency on initial condition.

A near future prediction from the viewpoint of the deterministic dynamical system is based on the Takens' theorem for "reconstructing the attractor in the state space and of the original dynamical system from single observed time series data". The Takens+ theorem is summarized below.

From the observed time series data y(t), a vector x(t) is generated as follows.

$$x(t)=(y(t), y(t-\tau), y(t-2\tau), \ldots, y(t-(n-1)\tau))$$

where "$\tau$" represents a time delay. This vector indicates one point of an n-dimensional reconstructed state space $R^n$. Therefore, it is possible to draw trajectory in the n-dimensional reconstructed state space by changing "T". Assuming that the target system is a deterministic dynamical system and that the observed time series data is obtained through an observation system corresponding to $C^1$ continuous mapping from the state space of dynamical system to the 1-dimensional Euclidean space R, the reconstructed trajectory is an embedding of the original trajectory when "n" value is sufficiently large.

Namely, if any attractor has appeared in the original dynamical system, another attractor, which remains the phase structure of the first attractor, will appear in the reconstructed state space. "n" is usually called an "embedding dimension".

In order that such reconstruction achieves "embedding", it has been proven that the dimension "n" should satisfy the following condition, where "m" represents the state space dimension of the original dynamical system.

$$n \geq 2m+1$$

However, this is a sufficient condition. Depending on data, embedding can be established even when "n" is less than 2m+1. Further, if n is greater than 2d (n>2d) where d is a box count dimension of the attractor in the original dynamical system, it is proven that the reconstructing operation becomes an one-by-one projection.

Since it has been proved that the change of the blood glucose level is a deterministic chaotic phenomenon, it is possible to predict a near future value of the blood glucose level on the basis of an attractor which is reconstructed in a reconstruction state space on the basis of the treatment of the time series data of the blood glucose level according to the Takens' embedding theorem.

Figure 5A:
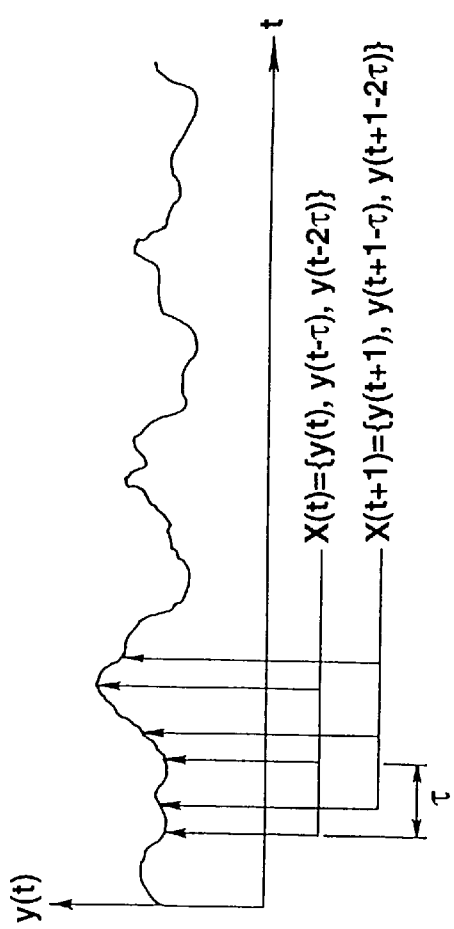
FIGS. 5A and 5B are explanatory views for explaining embedding of the time series data on a n-dimensional reconstruction space.

Concretely, the blood glucose time series data y(t) observed at constant sampling time intervals is embedded in an n-dimensional state space with the embedding dimension n and the time delay $\tau$ by the Takens' embedding theorem, as shown in FIG. 5A. This process is called "reconstruction". Consequently the following vector is obtained.

$$x(t)=(y(t), y(t-\tau), y(t-2\tau), y(t-(n-1)\tau))$$

wherein j=1~L, L is the numbers of data of time series data y(t).

Figure 5B:
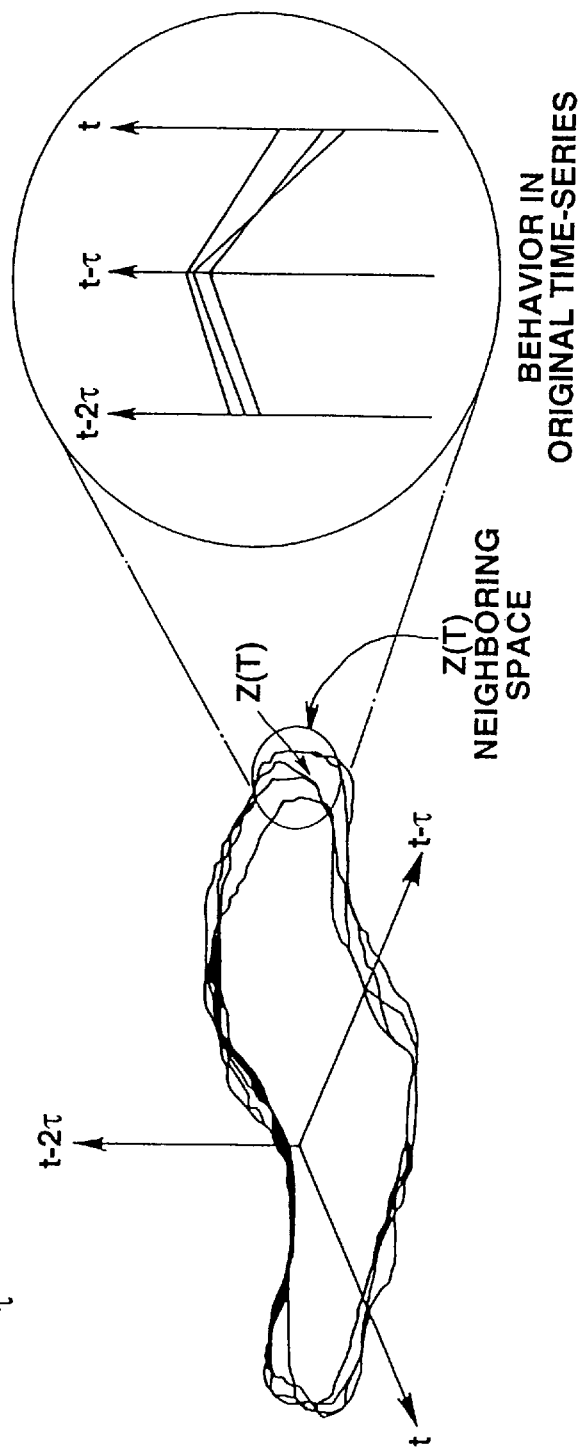

When this reconstruction is repeated on a number of observed data, a smooth manifold consisting of a finite number of data vectors can be composed in the n-dimensional reconstructed state space. FIG. 5B shows the attractor trajectory obtained by embedding the time series data into three-dimensional reconstructed state space.

With regard to the state space and attractor trajectory reconstructed by the embedding procedure, the near-feature trajectory of the data vector including the latest time series observed is presumed by using each trajectory of that data vector and the neighboring on, thereby determining the vector at s step ahead. That is, it is possible to obtain a predicted value of the blood glucose level in a near future from the present blood glucose data vector and the neighboring data vector thereof.

Figure 6:
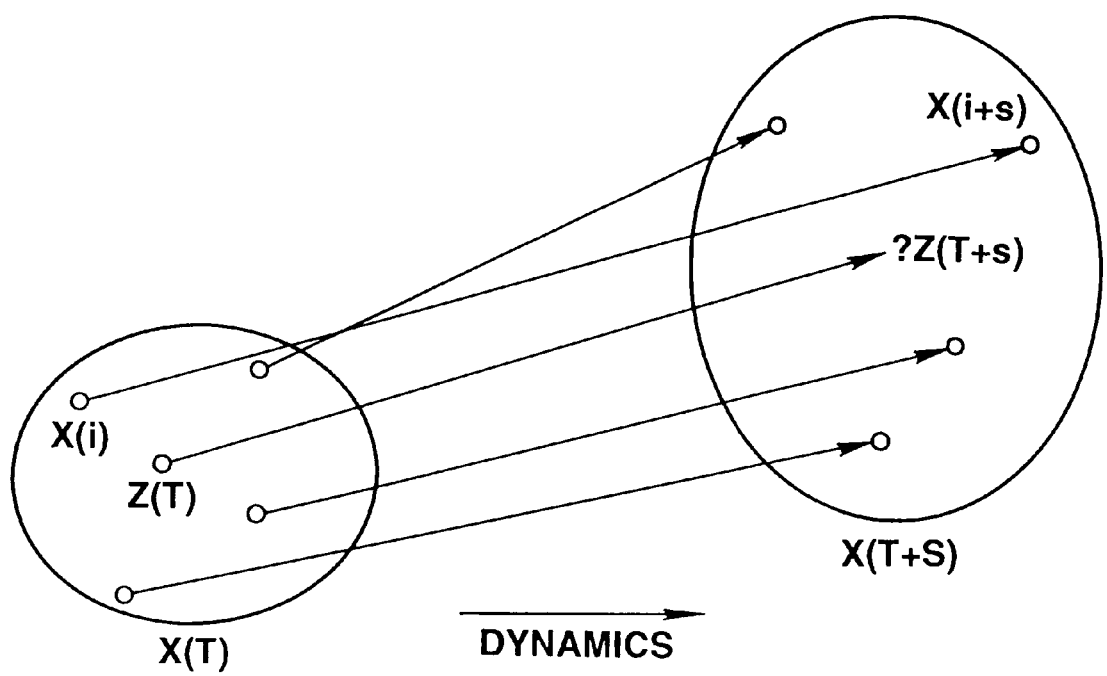
FIG. 6 is an explanatory view for explaining a dynamics from x(T) to x(T+s) by means of the Local Reconstruction Method.

By plotting the data vector z(T) resulting from the latest observation in the n-dimensional reconstructed state space and by replacing the neighboring data vector with x(i), the state x(i+s) at s steps ahead is already known as shown in FIG. 6 because x(i) is the past data. By using this, the predicted value z(T+s) at s steps ahead with respect to the present deta vector z(T) is obtained. Further, the predicted value y(t+s) at s steps ahead with respect to the original time series data is obtained from this predicted value z(T+s).

(Blood Glucose Level Prediction by Local Fuzzy Reconstruction Method)

In the prediction of the blood glucose level by means of the local reconstruction method, the transition from state x(i) to state x(i+s) after s steps can be assumed to be dependent on the dynamics subjected to determinism, wherein i∈N(z(T)), and N(z(T)) are the set of index i of x(i) neighboring z(T). This dynamics can be described in the form below.

$$\text{IF } x(T) \text{ is } x(i) \text{ THEN } x(T+s) \text{ is } x(i+s) \tag{1}$$

where x(i) is a set of the data vector neighboring z(T) in the n-dimensional reconstruction state space, x(T+s) is a set representative of a data vector at s step ahead x(T), and x(i) is a data vector neighboring to x(T). Therefore, if the step S is a time when the deterministic causality is still remained due to the sharp dependency to an initial value of the chaos, it can be assumed that the dynamics from the transition form state z(T) to state z(T+s) is approximately equivalent to that from state x(i) to x(i+s).

When the attractor embedded in the n-dimensional reconstructed state space is smoothly manifold, the trajectory from x(T) to x(T+s) is influenced by the vector distance from x(T) to x(i). That is, it can be deemed that the trajectory of x(i) affects the trajectory from z(T) to z(T+s) according to the decrease of the distance of the x(t) to z(T).

As mentioned above, the following relations are established.

$$x(i)=(y(i), y(i-\tau), y(i-2\tau), y(i-(n-1)\tau))x(i+s)=(y(i+s), y(i+s-\tau), y(i+s-2\tau), y(i+s-(n-1)\tau)) \tag{2}$$

This formula can be rewritten as follows when focusing attention on the j axis in the n-dimensional reconstructed state space.

$$\text{IF } aj(T) \text{ is } yj(i) \text{ THEN } aj(T+s) \text{ is } y(i+s) \ (j=1\sim n) \tag{3}$$

where aj(T) is the J-axis component of the neighboring value x(i) to z(T) in n-dimensional reconstructed state space, aj(T+s) is the J-axis component of x(i+s) in n-dimensional reconstruction state space, and n is the dimension of embedding.

Also, the trajectory from x(T) to X(T+s) is influenced by vector distance from z(T) to x(i). The attractor corresponding to the trajectory of the vector is a smooth manifold, and therefore this influence is represented by a nonlinear form. Hence, for rending a nonlinear characteristic, the formula (3) can be expressed by the fuzzy function as follows:

$$\text{IF } aj(T)=\tilde{y}j(i) \text{ THEN } aj(T+s)=\tilde{y}j(j+s) \ (j=1\sim n) \tag{4}$$

Further, the following formula has been already established.

$$z(T)=(y(T, y(T-\tau), y(T-2\tau), y(T-(n-1)\tau))$$

Therefore, the j-axis component of z(T) in the n-dimensional reconstructed state space becomes equal to yj(T).

Accordingly, the j-axis component of the predicted value ẑ(T+s) of data vector z(T+s) after s steps of z(T) is obtained as aj(T+s) by the fuzzy inference with yj(T) substituted into aj(T) of formula (6). This method is called the Local Fuzzy Reconstruction Method.

Explanation thereof is given below in a concrete example where the dimension are of embedding n=3, the time delay τ=4, and the number neighboring data vectors N=3. Let us assume each data vector as follows:

$$z(T)=(y1(T), y2(T-4), y3(T-8))$$

$$x(a)=(y1(a), y2(a-4), y3(a-8))$$

$$x(b)=(y1(b), y2(b-4), y3(b-8))$$

$$x(c)=(y1(c), y2(c-4), y3(c-8))$$

$$\hat{z}(T+s)=(y1(T+s), y2(T+s-4), y3(T+s-8))$$

$$x(a+s)=(y1(a+s), y2(a+s-4), y3(a+s-8))$$

$$x(b+s)=(y1(b+s), y2(b+s-4), y3(b+s-8))$$

$$x(c+s)=(y1(c+s), y2(c+s-4), y3(c+s-8))$$

where x(a), x(b) and x(c) are neighboring data vectors to z(T). x(a+s), x(b+s) and x(c+s) are data vectors s step ahead of x(a), x(b) and x(c), respectively.

On this assumption, the fuzzy rule given in formula (4) can be represented by formulas (5) to (7).

Regarding the first axis of reconstructed state space,

IF $a1(T)$ is $\tilde{y}1(a)$ THEN $a1(T+s)$ is $\tilde{y}1(a+s)$

IF $a1(T)$ is $\tilde{y}1(b)$ THEN $a1(T+s)$ is $\tilde{y}1(b+s)$

IF $a1(T)$ is $\tilde{y}1(c)$ THEN $a1(T+s)$ is $\tilde{y}1(c+s)$ (5)

Regarding the second axis of the reconstructed state space,

IF $b2(T)$ is $\tilde{y}2(b-4)$ THEN $a2(T+s)$ is $\tilde{y}2(a+s-4)$

IF $b2(T)$ is $\tilde{y}2(a-4)$ THEN $a2(T+s)$ is $\tilde{y}2(b+s-4)$

IF $a2(T)$ is $\tilde{y}2(c-4)$ THEN $a2(T+s)$ is $\tilde{y}2(c+s-4)$ (6)

Regarding the third axis of the reconstructed state space,

IF $a3(T)$ is $\tilde{y}3(a-8)$ THEN $a3(T+s)$ is $\tilde{y}3(a+s-8)$

IF $a3(T)$ is $\tilde{y}3(b-8)$ THEN $a3(T+s)$ is $\tilde{y}3(b+s-8)$

IF $a3(T)$ is $\tilde{y}3(c-8)$ THEN $a3(T+s)$ is $\tilde{y}3(c+s-9)$ (7)

Figure 7A:
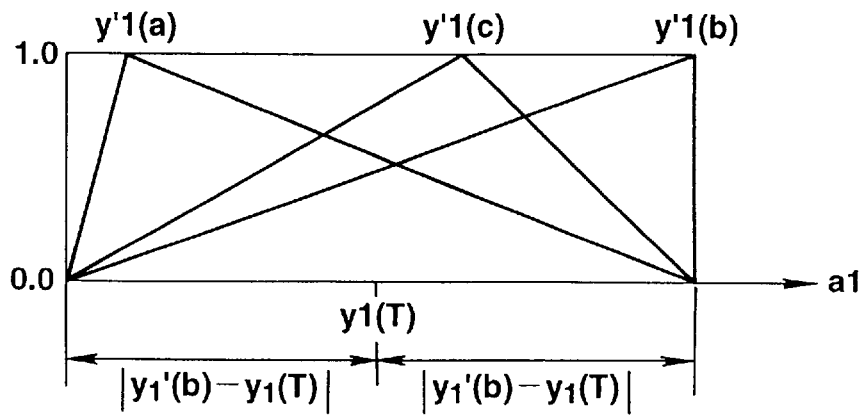
FIGS. 7A to 7C are graphs of membership functions in antecedent statement in the Local Fuzzy Reconstruction Method.
Figure 7B:
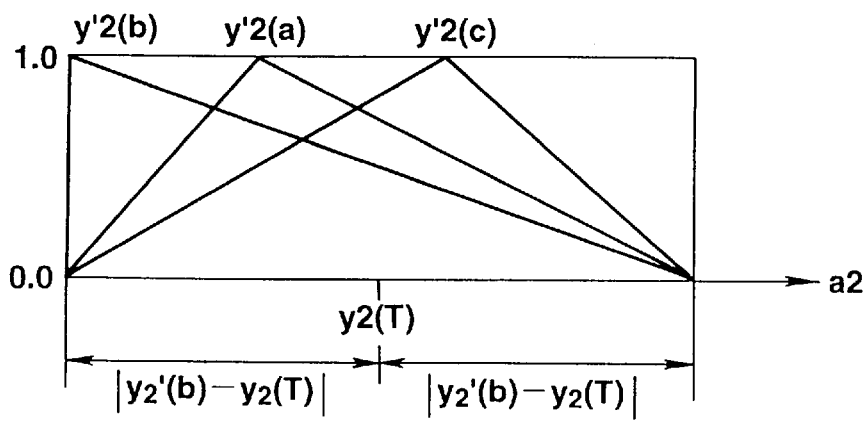
Figure 7C:
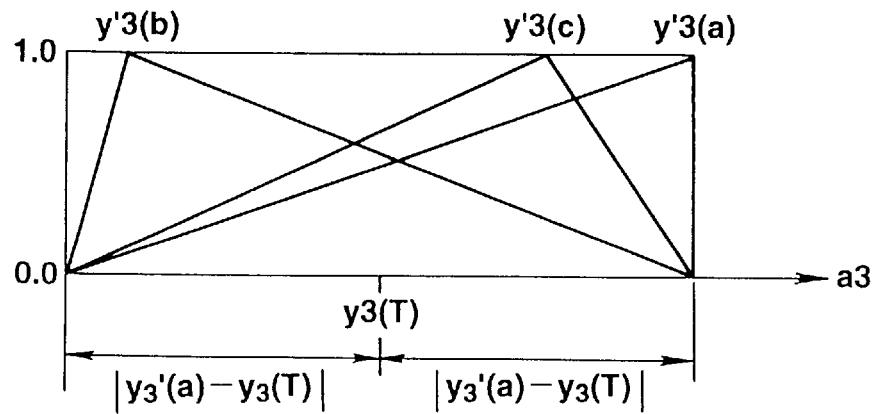

As shown in FIG. 7, a1(T), a2(T) and a3(T) represent the first, second and third axes at step T, and a1(T+s), a2(T+s)

and a3(T+s) represent the respective axes at step T+s. Because x(a), x(b) and x(c) are neighboring data vectors around z(T), each axis of the reconstructed state space in the antecedent statement of fuzzy rule (5), (6) and (7) has the membership function shown in FIG. 7. Note that the membership functions in the subsequent are all of a crisp expression.

For the dynamics expressed by the above fuzzy rules and membership functions, a fuzzy influence is conducted with the following taken as input data:

$$a1(T)=y1(T),\ a2(T)=y2(T),\ a3(T)=y3(T).$$

In consequence, the following formula is obtained.

$$\hat{y}1(T+s)=a1(T+s)$$
$$\hat{y}2(T+s)=a2(T+s)$$
$$\hat{y}3(T+s)=a3(T+s) \qquad (8)$$

Thus, the predicted value $\hat{y}1(T+s)$ at s steps ahead of the original time series data y1(T) is obtained as a1(T+s).

As mentioned above, by utilizing the interpolation ability and the local approximating ability of the Fuzzy Inference, the predicted value z(T+s) is obtained. From this predicted value z(T+s), a predicted value y(t+s) after s steps can be obtained.

In order to adapt the prediction employing the Local Fuzzy Reconstruction Method to the prediction of the blood glucose level, the following steps are executed: obtaining the data vector z(T) of the present blood glucose level from an attractor constructed by embedding the time series data of the blood glucose level in the multidimensional state space, obtaining a plurality of neighboring vectors x(i) on the other trajectory passing through a neighbor space of the data vector z(T) on the basis of a selecting reference that the Euclidean distance is small, obtaining a data vector x(i+s) at s steps future with respect to the data vector x(i) from the attractor, obtaining a predicted value z(T+s) at s steps future with respect to the data vector z(T) by using the data vectors z(T), x(i) and x(i+s) by means of the Local Fuzzy Reconstruction Method; and obtaining a time series blood glucose level predicted value y(t+s) at s steps future with respect to the predicted value z(T+s).

(Prediction Experiments Under the Local Fuzzy Reconstruction Method)

The inventors of the present invention found that it is possible to predict the blood glucose time series behavior in the near future by adapting the blood glucose level measurement data into the chaos theorem, by means of various experiments.

Figure 8:
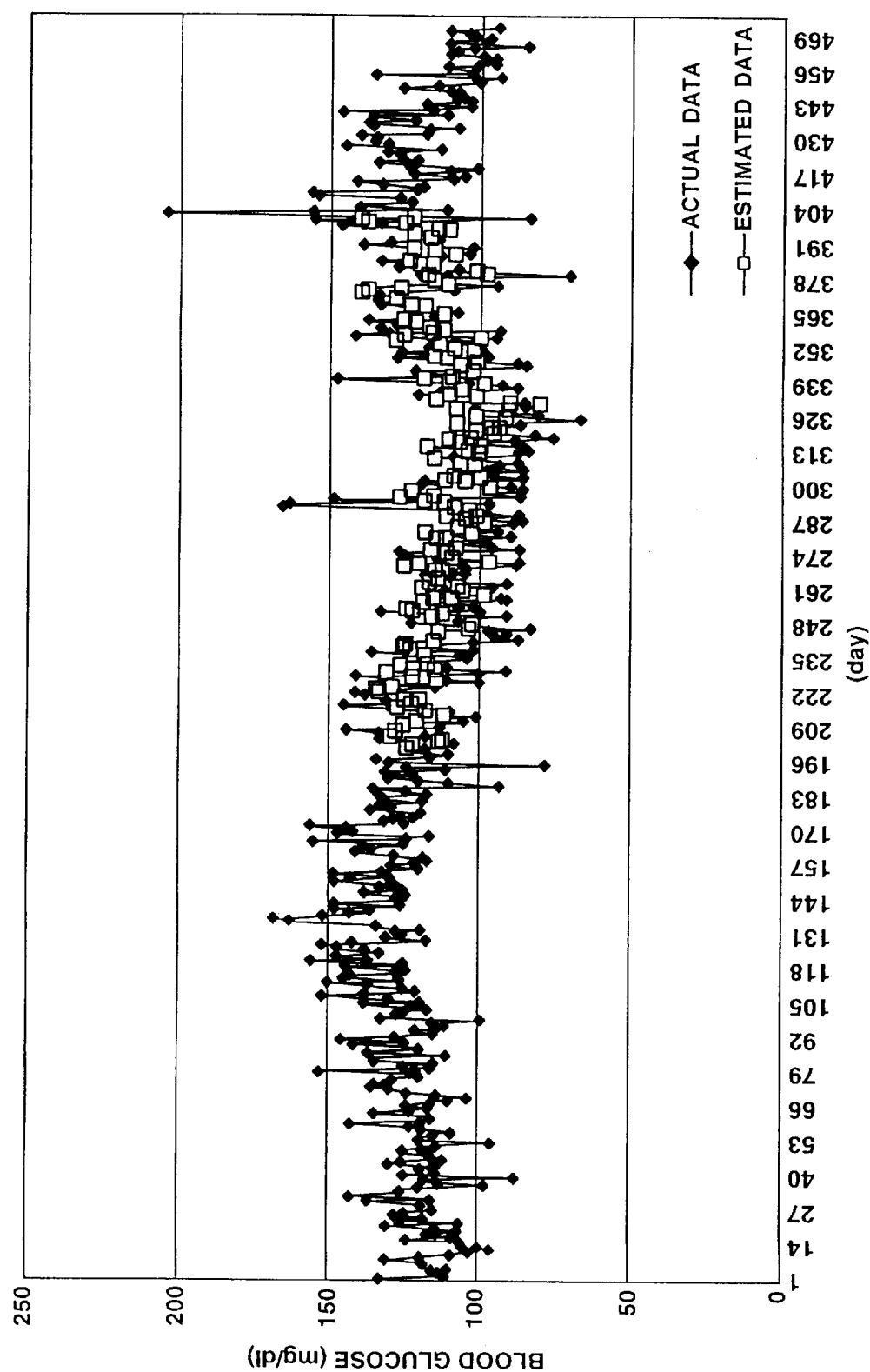
FIG. 8 is a graph showing a prediction result of the case I.

The experiments were to execute a blood glucose level prediction in one-day future of each case by using a software employing the Local Fuzzy Reconstruction Method. The prediction result obtained in the experiment was shown in FIG. 8 upon being compared with actual measurement data. FIG. 8 shows a result as to the case I. As is clear from the data, the prediction was executed with an error less than 20 mg/dl in average. This result proved that this prediction had an accuracy applicable to a practical use. The good results were obtained at to the other cases.

From the prediction result, when the prediction result is smaller than a predetermined level, by preparing a proper program form slightly changing the insulin administration amount which effectively functions at this timing, it becomes possible to construct a best mode blood glucose level control system without time lag.

(System for Predicting Near Future Blood Glucose Level by the Local Fuzzy Reconstruction Method)

Figure 1:
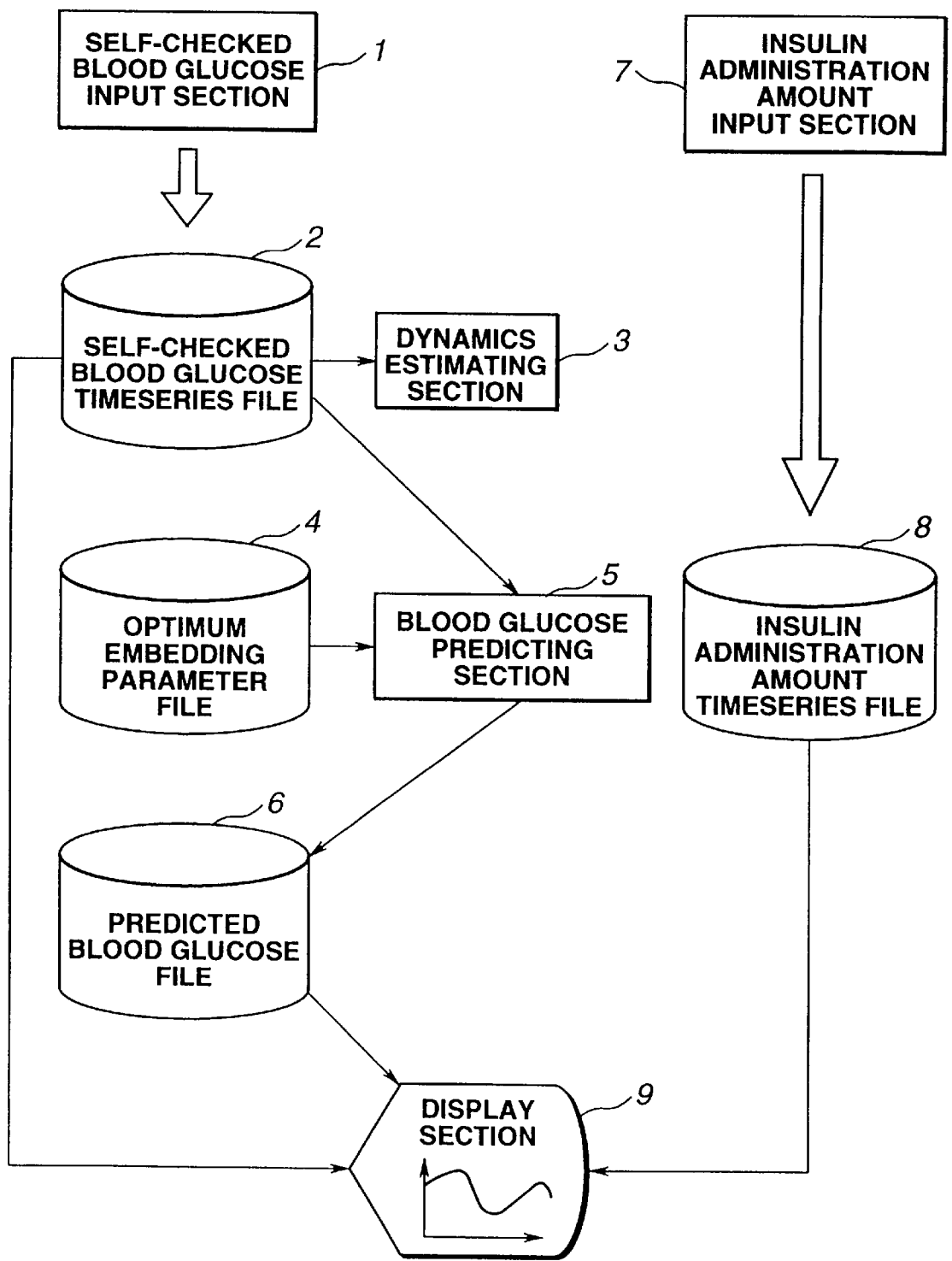
FIG. 1 is a structural view showing a blood glucose level predicting system of an embodiment according to the present invention.

FIG. 1 shows a system structural view of the blood glucose level predicting system according to the present invention.

A self-checked blood glucose input section 1 shown in FIG. 1 sends a measurement value of the blood glucose level measured by a diabetic day by day by means of a communication means such as internet communication, PHS (personal handy-phone system), on-line personal computer communication, pocket pager, or facsimile. A blood glucose time series file 2 is a part of an external storage system of a computer system equipped in a medical center. The blood glucose time series file 2 stores the self-checked blood glucose data sent from the blood glucose input section 1 as time series data by each patient. A dynamics estimating section 3 estimates a dynamics which most preferably represents a phase characteristic of each time series data stored in the file 2. The estimation of the dynamics is executed to predict one step future functioning as a parameter for embedding into a multi-dimensional state space, that is, an initial value for embedding an early half of the file by each patient. The dynamics estimating section 3 executes to predict one step future value in case that the data of early half plus one (early half+1) is known. After the reputation of this process until a newest data, the best performance process is selected, and "the embedding dimension n" and "the time delay $\tau$" of the best performance process are selected.

The estimation of the dynamics is executed when the self-checked data is damped to a predetermined amount and when the predicting performance is degraded due to the change of the dynamics such that the change of the blood glucose level of the patient moved from poor control to fair control or good control.

The optimum embedding parameter file 4 stores "the embedding dimension n" and "the time delay $\tau$" obtained at the dynamics estimating section 3 as a parameter for each patient.

The blood glucose predicting section 5 executes a prediction of the blood glucose level at 1 to s step ahead (future) in such a manner to pick up the blood glucose level measurement data of a selected patient from the blood glucose time series file 2, to select an optimum embedding parameter corresponding to the picked-up data from the parameter file 4, and to predict the near future value of the blood glucose level on the basis of the selected data and the parameters by means of the Local Fuzzy Reconstruction Method.

The prediction of the blood glucose level by the above-mentioned system according to the present invention is executed by the following manner: preparing measured data of blood glucose level (newest latest and past) for use as time series data; constructing an attractor by embedding the time series data in a multidimensional space according to the Takens' embedding theorem; selecting data vector z(T) on the attractor which vector (attractor) includes the latest blood glucose level data; selecting a plurality of neighboring vectors x(i) on the other trajectory passing through a neighbor space of the data vector z(T) on the basis of a selecting reference that the Euclidean distance is small; selecting a data vector x(i+s) at s steps future with respect to the data vector x(i) from the attractor; estimating (inferring) a predicted value z(T+s) at s steps future with respect to the data vector z(T) by using the data vectors z(T), x(i) and x(i+s) by means of the Local Fuzzy Reconstruction Method; and obtaining a predicted value y(T+s) at s step future with respect to the predicted value z(T+s).

A predicted blood glucose file 6 stores the blood glucose level dada predicted at the blood glucose predicting section 5 for each patient. An insulin administration amount input section 7 sends the amount of the insulin practically administrated to the patient, by means of a communication means such as internet, PHS, on-line personal computer communication, packet pager, or facsimile to a medical center. An insulin administration amount time series file 8 is a part of an external storage system of a computer system equipped in the medical center. The insulin administration amount time series file 8 stores the insulin administration amount data sent from the insulin administration amount input section 7 as time series data by each patient. A display section 9 displays data for each patient upon searching the data from the blood glucose time series file 2, the predicted blood glucose file 6 and the insulin administration amount time series file 8 to provide necessary information for the treatment for diabetic to a doctor. The display section 9 also displays information representative of degree of certainty of the prediction and degree of errors of the prediction, in addition to the present actual value of the blood glucose level, the near future predicted value of the blood glucose level and a history of the insulin administration.

With the thus arranged system, it is possible that a doctor decides a proper insulin administration amount from the predicted blood glucose level based on the dynamics of the change of the blood glucose level of each patient. This realizes a time lag less control of blood glucose level. Therefore, it is possible to keep the change of the blood glucose level within an allowable range in a long period while decreasing the magnitude of the change of the blood glucose level by each day. Further, it is possible that a patient positively utilizes the self-checked data and a doctor provides a daily instruction to the patient on the basis of the predicted blood glucose level. This functions that the patient improves motivation as to the self-check of the blood glucose level.

It will understood that a recording medium storing the blood glucose level predicting method according to the present invention may be utilized in various microcomputers to assist insulin therapy for diabetics.

The contents of Japanese Patent Application No. 10-93783, with a filing date of Apr. 7, 1998 in Japan, are hereby incorporated by reference.

What is claimed is:

1. A system for predicting a blood glucose level comprising:
    a time series measurement data storing means for storing blood glucose level measured data in a blood glucose time series file to treat the data as time series data;
    a dynamics estimating means for estimating a dynamics which most preferably represents a phase characteristic of the time series data stored in said time series measurement data storing means;
    a parameter storing means for storing an embedding dimension n and a time delay τ of the dynamics estimated in said dynamics estimating means as parameters for embedding the estimated dynamics in a multidimensional state space;
    a blood glucose predicting means for predicting a near future value of the blood glucose level by means of the Local Fuzzy Reconstruction Method on the basis of the data of the blood glucose level stored in the blood glucose time series file and the parameters corresponding to the data, said blood glucose predicting means storing the predicted future value in a predicted blood glucose level file; and
    a display means for displaying the data of the blood glucose time series file and the predicted blood glucose file.

2. A method for predicting blood glucose level comprising the steps of:
    preparing blood glucose level data measured at latest time and past time for use as time series data;
    constructing an attractor by embedding the time series data in a multidimensional state space according to the Takens' embedding theorem;
    selecting a data vector z(T) on the attractor which includes the latest blood glucose level data;
    selecting a plurality of neighboring vectors x(i) on the other trajectory passing through a neighbor space of the data vector z(T) on the basis of a selecting reference that the Euclidean distance thereof is smaller that a predetermined value;
    selecting a data vector x(i+s) at s steps future with respect to the data vector x(i) from the attractor;
    estimating (inferring) a predicted value z(T+s) at s steps future with respect to the data vector z(T) by using the data vectors z(T), x(i) and x(i+s) by means of the Local Fuzzy Reconstruction Method; and
    obtaining a predicted blood glucose level y(T+s) at s step future on the basis of the predicted value z(T+s).

3. A method as claimed in claim 2 further comprising a step for displaying the predicted value z(T+s).

4. A method as claimed in claim 2 stored in a medium usable in a microcomputer.

5. A system for predicting a blood glucose level comprising:
    a self-checked blood glucose input section sending a self checked value of blood glucose level measured by a diabetic at predetermined intervals;
    a blood glucose time series file storing the self-checked blood glucose data sent from said blood glucose input section as time series data by each patient;
    a dynamics estimating section estimating,a dynamics which most preferably represents a phase characteristic of each time series data stored in said blood glucose time series file;
    an optimum embedding parameter file storing an embedding dimension and a time delay obtained at said dynamics estimating section as parameters for each patient;
    a blood glucose predicting section executing a prediction of the blood glucose level at a near future on the basis of the selected data and the parameters by means of the Local Fuzzy Reconstruction Method;
    a predicted blood glucose file storing the blood glucose level dada predicted at said blood glucose predicting section for each patient;
    an insulin administration amount input section sending the amount of the insulin practically administrated to the patient;
    an insulin administration amount time series file storing the insulin administration amount data sent from said insulin administration amount input section as time series data by each patient; and
    a display section displaying data for each patient upon searching the data from said blood glucose time series file, said predicted blood glucose file and said insulin administration amount time series file to provide necessary information for the treatment for diabetic to a doctor.

6. A system as claimed in claim 5 wherein the self-checked blood glucose data is sent from said blood glucose input section by means of a communication means which includes internet communication, personal handy-phone system, on-line personal computer communication, pocket pager, and facsimile.

* * * * *

UNITED STATES PATENT AND TRADEMARK OFFICE
CERTIFICATE OF CORRECTION

PATENT NO. : 5,971,922
DATED : October 26, 1999
INVENTOR(S) : Zeizaburou ARITA, et al.

It is certified that error appears in the above-indentified patent and that said Letters Patent is hereby corrected as shown below:

Title page, item [73] Assignee: KABUSHIKI KAISHA MEIDENSHA, Tokyo, Japan; Seizaburou ARITA, Kobe-shi, Japan; Masaya YONEDA, Okayama-shi, Japan.

Signed and Sealed this

Twenty-sixth Day of December, 2000

Attest:

Q. TODD DICKINSON

*Attesting Officer*    *Director of Patents and Trademarks*